United States Patent [19]

Crainich

[11] Patent Number: 4,607,638
[45] Date of Patent: Aug. 26, 1986

[54] SURGICAL STAPLES

[75] Inventor: Lawrence Crainich, Stratford, Conn.

[73] Assignee: Design Standards Corporation, Bridgeport, Conn.

[21] Appl. No.: 602,406

[22] Filed: Apr. 20, 1984

[51] Int. Cl.[4] .............................................. A61B 17/04
[52] U.S. Cl. ................................... 128/335; 411/472; 411/499
[58] Field of Search ............... 128/334 R, 335, 339, 128/337, 336; 411/457, 472, 471, 494, 499; 604/239

[56] References Cited

U.S. PATENT DOCUMENTS

| | | | |
|---|---|---|---|
| 517,836 | 4/1894 | Bradish | 411/472 X |
| 527,184 | 10/1894 | Richey | 411/472 X |
| 3,094,123 | 6/1963 | Kurtz | 128/339 |
| 3,605,402 | 9/1971 | Larson | 411/457 X |
| 4,127,227 | 11/1978 | Green | 411/457 X |
| 4,261,244 | 4/1981 | Becht et al. | 128/334 R X |
| 4,403,693 | 9/1983 | Froehlich | 411/457 X |
| 4,407,286 | 10/1983 | Noiles | 411/457 X |

FOREIGN PATENT DOCUMENTS

| | | | |
|---|---|---|---|
| 2738452 | 10/1978 | Fed. Rep. of Germany | 128/339 |
| 707661 | 4/1931 | France | 411/457 |
| 2481930 | 11/1981 | France | 604/239 |
| 475574 | 11/1952 | Italy | 411/457 |
| 82/00582 | 3/1982 | World Int. Prop. O. | 128/334 R |
| 434937 | 11/1974 | U.S.S.R. | 128/339 |

OTHER PUBLICATIONS

Bickham, Operative Surgery, 1924, p. 368, FIGS. 1411-1413.

Primary Examiner—Paul E. Shapiro
Attorney, Agent, or Firm—Bachman & LaPointe

[57] ABSTRACT

Surgical staples having improved configurations providing significant advantages such as parallel stacking, square bending, easier skin penetration due to sharp point, and others.

12 Claims, 11 Drawing Figures

SURGICAL STAPLES

BACKGROUND OF THE INVENTION

Surgical staples to close incisions or wounds in body tissue are well known in the art, as are surgical stapling apparatus for applying the staples, for example, see U.S. Pat. Nos. 4,014,492, 4,043,504, 4,265,226, 4,375,866, 4,399,810 and 4,407,286.

The surgical staples have a U-shaped configuration with an elongated or broad base portion, relatively square or slightly curved corners and two relatively shorter legs perpendicular to the base connected thereto at the corners and terminating at the other end in a sharpened, skin-piercing point. The staples are typically applied by a stapling apparatus wherein a group of same are held in the apparatus and advanced toward an anvil by a staple pusher having an end with a generally U-shaped recess. The base of the U-shaped recess in the staple pusher is broader than the anvil, but not as broad as the base of the U-shaped staple. When the staple reaches the anvil, the staple pusher causes the staple to bend or be deformed around the anvil into an open-sided, substantially O-shaped configuration by bending the staple at two points along the elongated base portion. This procedure can be referred to as forming the staple. As this is taking place the sharpened points of the staple enter the tissue on opposite sides of the incision or wound and draw the tissue together. When the staple has been fully formed the staple pusher is retracted and the stapler is removed by sliding the anvil out from within the staple. The staple remains within the tissue to hold the tissue together during healing and is removed after healing by a staple remover.

It is desirable to provide improved surgical staple configurations. For example, surgical staples are formed by bending thin wire. Bending the wire to form the aforesaid relatively square corners causes a slight bulging which causes undesirable non-parallel stacking in the staple apparatus. Also, it is desirable to insure square bending and twist elimination in the staple forming procedure. In addition, it is highly desirable to provide a sharper skin-piercing point to reduce skin trauma. Further, it is desirable to promote ease of formed staple removal.

Accordingly, it is a principal object of the present invention to provide improved surgical staple configurations.

It is a further object of the present invention to provide improved surgical staple configurations which achieve significant advantages and overcome the deficiencies of staples known heretofore.

Further objects and advantages of the present invention will appear from the present specification.

SUMMARY OF THE INVENTION

In accordance with the present invention it has now been found that the foregoing objects and advantages may be readily obtained.

In a first embodiment of the present invention a surgical staple is provided having a U-shaped configuration and a substantially round cross-section and an elongated base portion and two legs substantially perpendicular to said base portion connected thereto at one end by a transition portion and terminating at the other end in a sharpened point, wherein at least a portion of said legs are bulged beyond the plane of said round cross-section, preferably bulged from 0.001" to 0.010" beyond the plane. By beyond the plane is meant wider than the original wire diameter which generally is in the range of 0.018" to 0.026". An advantage of this embodiment is that it promotes parallel stacking when the staples are loaded next to one another in a cartridge. In addition, it enables one to pick off one staple at a time from a stack of staples without disturbing the rest of the stack due to the small gap between the backspan or base portions of the staples.

In a further or second embodiment of the present invention the sharpened point is characterized by having greater than one (1) facet. Suitable examples of this include two (2) or three (3) facets, a rounded or semi-circular configuration with a radial nose, and two (2) facets combined with a radial nose. An advantage of this embodiment is that it develops a very sharp point for easier skin or tissue penetration and thereby reduces skin or tissue trauma.

In a still further or third embodiment of the present invention a surgical staple is provided having a U-shaped configuration, a substantially round cross-section and an elongated base portion and two legs substantially perpendicular to said base portion connected thereto at one end by a transition portion and terminating at the other end in a sharpened point. The staple is deformed in use into an open-sided, substantially O-shaped configuration bended at two (2) points along said elongated base portion. In accordance with this embodiment the base portion has an inner side at the center of the U (facing said legs) and an outer side opposed thereto and the elongated base portion has notched portions, preferably two (2), on the outer side at the locus of the elongated base portion bends spaced from each other and spaced from said transition portion. Preferably said notched portions are from 0.002" to 0.003" in depth. Advantages of this embodiment are the promotion of square bending in the forming operation without any resultant twist.

In a fourth embodiment of the present invention the staple has at least one flattened, work hardened area from 0.005" to 0.010" in depth along the surface of the staple. In an example of this embodiment the entire inside or inner side surface of the base portion or a portion thereof can be flattened and work hardened. Alternatively or in addition thereto the outer side of the elongated base portion can have three (3) flattened, work hardened portions spaced from each other by two (2) rounded portions at the locus of the base portion bends. A still further alternative alone or in combination with the above would be to provide flattened, work hardened portions on the legs. Naturally, this would provide the additional advantages of the first embodiment of the present invention. Advantages of this embodiment include the promotion of square bending and twist elimination as well as the advantages inherent in the work hardening operation. The work hardening is simply accomplished by the deep flattening procedure.

In the fifth or final embodiment of the present invention the elongated base portion is indented to form two (2) upstanding ears adjacent said transition portion separated by a lower ledge. The indentation is from 0.020" to 0.050" deep. In the formed staple the upstanding ears enhance ease of staple removal. In addition this embodiment obtains more advantageous forming.

Some or several of the embodiments of the present invention may of course be combined with one another based upon the particular circumstances.

BRIEF DESCRIPTION OF THE DRAWINGS

The present invention will be more readily understood from a consideration of the following illustrative drawings wherein.

DETAILED DESCRIPTION

Figure 1:
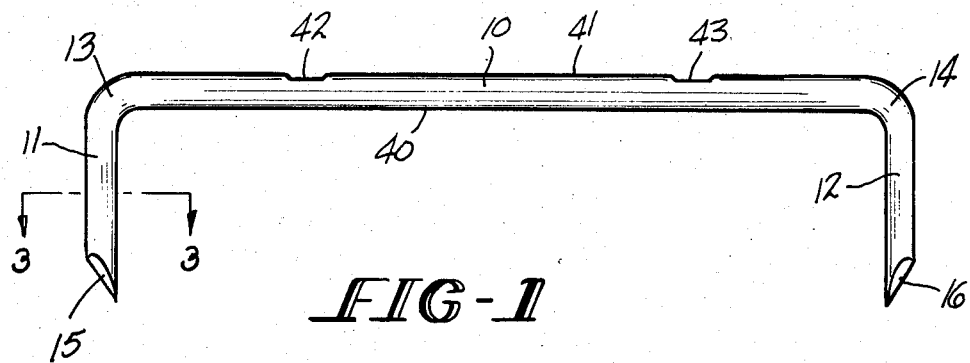
FIG. 1 is a side view of a staple of the present invention.
Figure 2:
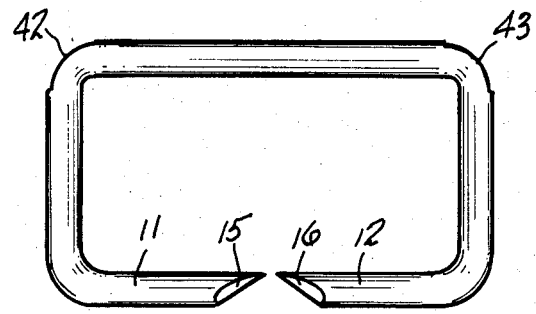
FIG. 2 is the staple of FIG. 1 after the forming procedure.
Figure 5:
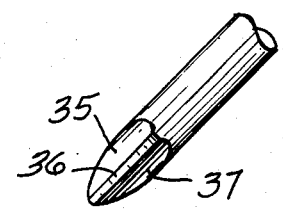
FIGS. 4, 5, 6 and 7 are enlarged perspective views of various embodiments of sharpened points, with FIG. 6 representing the conventional sharpened point.

Referring to the drawings, FIGS. 1 and 2 are side views of a surgical staple of the present invention, before and after forming, incorporating the features of embodiments 1, 2 and 3 discussed above. As can be seen in FIG. 1 (before forming) the staple has a U-shaped configuration and a substantially round cross-section, i.e., the staple is formed from wire, as for example, 316 L surgical stainless steel. The staple has an elongated base portion 10 and two legs 11 and 12 substantially perpendicular to the base portion. The legs are integral with the base portion and connected thereto at one end by a transition portion 13 and 14 which is slightly curved in shape. The legs terminate at the end opposed to the transition portion in sharpened points 15 and 16. As can be clearly seen in FIG. 1 the legs are substantially shorter than the base portion so that the combined length of both legs is shorter than the length of the base portion. In the forming operation the staple is deformed in use into the configuration shown in FIG. 2 into an open-sided, substantially O-shaped configuration bended at two points along said elongated base portion. As can be seen in FIG. 2, legs 11 and 12 are thereby bent inwardly so that sharpened points 15 and 16 face but do not touch one another.

Figure 3:
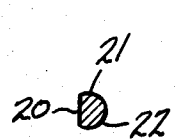
FIG. 3 is a cross-sectional view taken on line III—III of FIG. 1.

In a first embodiment of the present invention at least a portion of legs 11 and 12 are bulged beyond the plane of said round cross-section, i.e., bulged wider than the original wire diameter. This can be simply accomplished by flattening one side of each leg and preferably the entire legs. This can be clearly seen in FIG. 3 which shows flattened portion 20 and bulged side portions 21 and 22. In the conventional staple formation of the transition portion causes a slight outward bulging. This tends to result in the staples bowing somewhat when stacked in an accordion-like condition. The leg flattening feature of the present invention promotes parallel stacking when the staples are loaded next to one another and eliminates the accordion condition when the staples are fed from a magazine. Also, the leg flattening feature creates a gap between the respective base portions or backspan of the staples and enables one to pick off one staple at a time due to the gap without disturbing the rest of the stack. The bulge in the legs is from 0.001" to 0.010" wider than original wire diameter or beyond the plane of the round cross-section. Naturally, more than one side can be flattened or an oval configuration can be used. As indicated above, preferably an entire outside surface of both legs are coined.

Figure 4:
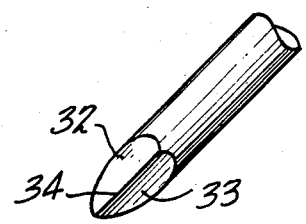
Figure 7:
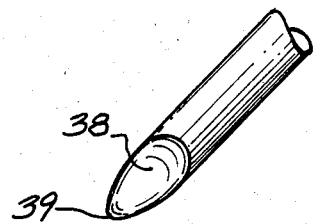
Figure 6:
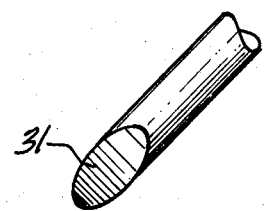

A second embodiment of the present invention is also shown in FIGS. 1 and 2 and illustrated in detail in FIGS. 4–7. In accordance with this embodiment sharpened points 15 and 16 are characterized by having greater than one facet. The conventional sharpened point is illustrated in FIG. 6 which shows a single sharpened facet 31 wherein the end portion of the leg is simply cut on a single line. In accordance with the embodiment of FIG. 4 two facets 32 and 33 are employed resulting in a much sharper point. The sharper point enables easier skin or tissue penetration with a resultant reduction in skin or tissue trauma. As can be seen in FIG. 4 facets 32 and 33 meet in centerline 34. In accordance with the embodiment of FIG. 5 three facets 35, 36 and 37 are employed. The embodiment of FIG. 7 shows a rounded or semi-circular configuration 38 which results in a multi-faceted tip portion 39. For simplicity the embodiment of FIG. 4 is preferred. Surprisingly the feature of this embodiment employing greater than one facet at the sharpened point very substantially increases the sharpness of the point portion.

The third embodiment of the present invention is also shown in FIGS. 1 and 2. In accordance with this embodiment it can be seen that base portion 10 has an inner side 40 facing legs 11 and 12 at the center of the U-shape and outer side 41 opposed thereto. The elongated base portion 10 has notched portions 42 and 43 along outer side 41 at the locus of the elongated base portion bends in the forming operation. This can be clearly seen in FIG. 2. Notched portions 42 and 43 are spaced from each other and spaced from transition portions 13 and 14. The notched portions have a depth of 0.002" to 0.003" and serve the function of creating a flat on the outside of the bend area which promotes square bending of the staple without any resultant twist.

Figure 8:
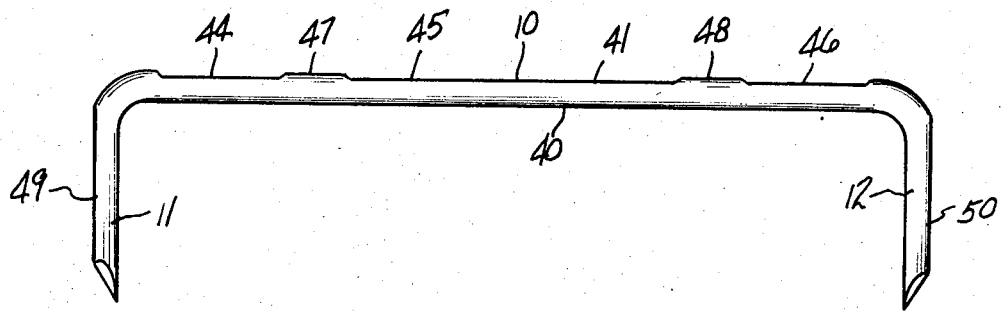
FIGS. 8 and 9 are side views of the fourth embodiment of the present invention before and after the forming operation, respectively.
Figure 9:
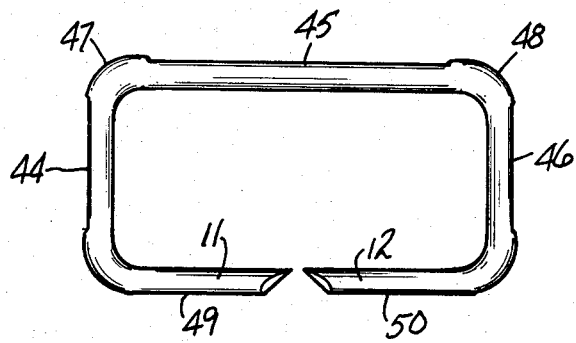

The fourth embodiment of the staple of the present invention is shown in FIGS. 8 and 9 which shows the staple before and after the forming operation. In accordance with this embodiment the staple has at least one flattened, work hardened area from 0.005" to 0.10" in depth along the surface of the staple. This work hardened area is normally formed by a coining operation. Thus, as clearly shown in FIG. 8 outer side 41 of base portion 10 has three (3) flattened, work hardened portions 44, 45 and 46 spaced from each other by two (2) rounded portions 47 and 48. Rounded portions 47 and 48 represent the original wire diameter or round cross-section and are situated at the locus of the bends in the forming operation as shown in FIG. 9. In addition, flattened, work hardened areas can be formed on legs 11 and 12 as shown by flattened, work hardened areas 49 and 50 on legs 11 and 12, respectively. Naturally flattened, work hardened areas 49 and 50 will also provide the advantages of the first embodiment of the present invention and serve to promote parallel stacking in accordance with an advantage of said first embodiment. The flattened, work hardened features promote square bending and twist elimination as well as the advantages inherent in the work hardening operation. By leaving rounded portions 47 and 48 one does not interfere with the easy forming operation necessary to transform the staple of FIG. 8 into the formed staple of FIG. 9. Thus, the uncoined or unhardened areas 47 and 48 are softer than the coined or work hardened areas in order to promote easy bending without fracture. As indicated above, the work hardening results in a generally stronger staple, which is highly advantageous in use, while achieving the other advantages referred to hereinabove. This is achieved while softer areas 47 and 48 readily stretch around the bend area without fracture.

Figure 10:
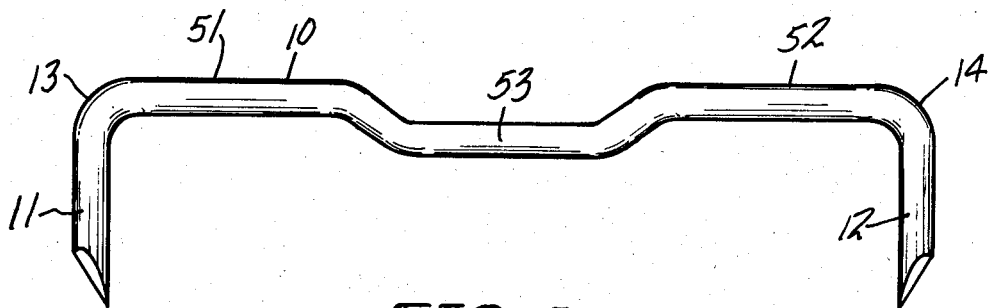
FIGS. 10 and 11 are side views of the fifth embodiment of the present invention before and after the forming operation, respectively.
Figure 11:
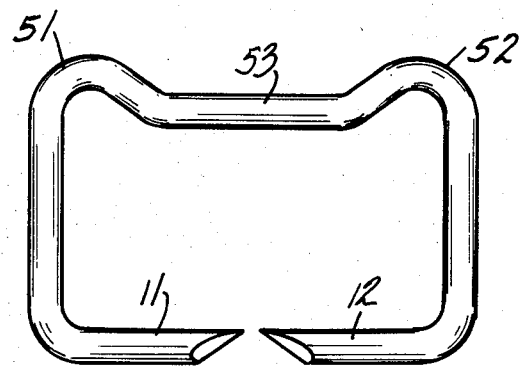

The fifth embodiment of the present invention is shown in FIGS. 10 and 11 which show the staple before and after forming, respectively. In this embodiment, elongated base portion 10 is indented to form upstanding ears 51 and 52 adjacent transition portions 13 and 14 separated by a lower ledge 53. The indentation of lower ledge 53 is from 0.020" to 0.050" deep. In the formed staple shown in FIG. 11 upstanding formed projections 51 and 52 enhance ease of staple removal, that is, ears 51 and 52 appear on the outermost portion of the staple. In the normal and conventional configuration the anvil and former will contact the center of the staple and might tend to cause rotating or rolling of the staple. This would produce a closure not flat and parallel. The depressed or indented feature of the fifth embodiment of the present invention overcomes rolling and results in projections in the formed staple for ease of removal. Thus, the removal device can readily sit in formed projections 51 and 52 in the formed staple.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A surgical staple having a U-shaped configuration and a substantially round cross-section and an elongated base portion and two legs substantially perpendicular to said base portion connected thereto at one end by a transition portion and terminating at the other end in a sharpened portion, wherein at least a portion of said legs are bulged beyond the plane of said round cross-section.

2. A staple according to claim 1 wherein said legs are flat sided.

3. A staple according to claim 1 wherein said legs are bulged from 0.001" to 0.010" beyond the plane.

4. A surgical staple having a U-shaped configuration and an elongated base portion and two legs substantially perpendicular to said base portion connected thereto at one end by a transition portion and terminating at the other end in a sharpened point, said staple being deformed in use into an open-sided substantially O-shaped configuration bended at two points along said elongated base portion, wherein said base portion has an inner side facing said legs and outer side opposed thereto and wherein said elongated base portion has flattened notched portions on the outside at the locus of the elongated base portion bends extending over the entire locus of the elongated base portion bends and spaced from each other and spaced from said transition portions.

5. A surgical staple according to claim 4 wherein said notched portions are from 0.002" to 0.003" in depth.

6. A surgical staple having a U-shaped configuration and a substantially round cross-section and an elongated base portion and two legs substantially perpendicular to said base portion connected thereto at one end by a transition portion and terminating at the other end in a sharpened portion, said staple being deformed in use into an open-sided substantially O-shaped configuration bended at two points along said elongated base portion, wherein said base portion has an inner side facing said legs and an outer side opposed to said legs and wherein said staple has at least one flattened, work hardened area from 0.005" to 0.010" deep along the surface of said staple.

7. A surgical staple according to claim 6 wherein said outer side of the base portion has three flattened, work hardened portions spaced from each other by two rounded portions at the locus of the elongated base portion bends.

8. A surgical staple according to claim 6 wherein the entire inside surface of said elongated base portion is flattened and work hardened.

9. A surgical staple according to claim 6 wherein said legs are flattened and work hardened.

10. A surgical staple having a U-shaped configuration and an elongated base portion and two legs substantially perpendicular to said base portion connected thereto at one end by a transition portion and terminating at the other end in a sharpened portion, wherein said elongated base portion is indented in an amount from 0.020" to 0.050" deep to form two upstanding ears adjacent said transition portion separated by a lower ledge.

11. A surgical staple according to claim 10 wherein said staple is deformed in use into an open-sided substantially O-shaped configuration bended at two points along said upstanding ears.

12. A surgical staple having a U-shaped configuration and an elongated base portion and two legs substantially perpendicular to said base portion connected thereto at one end by a transition portion and terminating at the other end in a sharpened point, wherein said sharpened point is characterized by having greater than one facet and has a rounded or semi-circular configuration with a radial nose.

* * * * *